US008000440B2

(12) United States Patent
Petch et al.

(10) Patent No.: US 8,000,440 B2
(45) Date of Patent: Aug. 16, 2011

(54) TARGET COMPOSITION DETERMINATION METHOD AND APPARATUS

(75) Inventors: Philip Edward Petch, Hamilton (NZ); Geordie Robert Burling-Claridge, Hamilton (NZ); Serguei Timofeevich Zavtrak, Hamilton (NZ); Martin Peter Upsdell, Hamilton (NZ)

(73) Assignee: Agresearch Limited, Hamilton (NZ)

( * ) Notice: Subject to any disclaimer, the term of this patent is extended or adjusted under 35 U.S.C. 154(b) by 119 days.

(21) Appl. No.: 12/307,811

(22) PCT Filed: Jul. 7, 2007

(86) PCT No.: PCT/NZ2007/000175
§ 371 (c)(1),
(2), (4) Date: Apr. 15, 2009

(87) PCT Pub. No.: WO2008/007976
PCT Pub. Date: Jan. 17, 2008

(65) Prior Publication Data
US 2009/0310744 A1    Dec. 17, 2009

(30) Foreign Application Priority Data

Jul. 10, 2006 (NZ) .................................. 548456
Oct. 27, 2006 (NZ) .................................. 550913

(51) Int. Cl.
*G01N 23/06* (2006.01)
(52) U.S. Cl. .......................................... 378/53; 378/57
(58) Field of Classification Search ............. 378/53, 378/57, 54, 56, 207
See application file for complete search history.

(56) References Cited

U.S. PATENT DOCUMENTS

| 3,965,358 | A | 6/1976 | Macovski ........................ 378/5 |
| 4,168,431 | A | 9/1979 | Henriksen ...................... 378/53 |
| 5,247,561 | A | 9/1993 | Kotowski ....................... 378/87 |
| 5,490,196 | A | 2/1996 | Rudich et al. ................ 378/101 |
| 2006/0109949 | A1 | 5/2006 | Tkaczyk et al. ................ 378/4 |
| 2007/0147585 | A1* | 6/2007 | Eilbert et al. .................. 378/57 |

FOREIGN PATENT DOCUMENTS

NZ    502033    6/2000
NZ    527573    3/2003

* cited by examiner

*Primary Examiner* — Courtney Thomas
(74) *Attorney, Agent, or Firm* — Greern, Burns & Crain, Ltd.

(57) ABSTRACT

A target composition determination apparatus includes, an x-ray emission element for concurrently transmitting x-ray photons with a plurality of different energy levels at a target, and an x-ray detection element for receiving x-rays interacting with the target and for determining the energy levels of the received x-rays, the x-ray detection element generating at least one output signal indicative of the number of x-rays interacting with the target and the energy levels determined for each of the x-rays, and a processing element receiving the output signal and indicating the presence of at least one component material within the target using the received detection element signal and a multivariate calibration prepared for the target, the apparatus including that the output signal of the x-ray detection element is batched over a pre-selected time period to define the physical resolution of the target composition apparatus when a target is moved relative to the apparatus.

23 Claims, 4 Drawing Sheets

TARGET COMPOSITION DETERMINATION METHOD AND APPARATUS

TECHNICAL FIELD

This invention relates to a method and apparatus configured to determine the composition of a target or at least the presence of at least one component material within a target. In a preferred implementation the present invention may employ x-ray spectra absorption information derived from a target, and may automatically act or issue a detection notification if one or more materials of interest are found to be present within a target.

BACKGROUND ART

In a number of instances it is important to detect or determine what are the component materials of an article with a non-invasive, fast and accurate process.

For example, security focussed detection systems are important equipment in the transport and travel industries. Such detection equipment is employed to deter and detect smuggling and terrorist activities. In particular, aircraft passenger luggage (both carry-on and hold-shipped) and air-freight needs to be assessed quickly by such systems to maintain a high turnover of departures and arrivals of aircraft from an airport. Aircraft passengers in particular dislike having their air travel delayed by security procedures.

The most effective of these security measures is a physical search of cargo or the passengers themselves to detect the presence of contraband, weapons and explosives. However, such physical searches are slow and also an invasive process for passengers which are to be avoided if possible.

Scanning based equipment is used to a limited extent in the form of x-ray absorption systems to scan luggage and cargo. X-rays have a strong penetrating power which can be used to examine an entire piece of luggage quickly. However, such x-ray absorption based systems provide only limited information with respect to the composition of a target or, in particular, a piece of luggage under investigation. Such existing x-ray security scanners can provide general information in terms of the physical outline of an article present within a target which strongly absorbs x-rays. In particular, dual energy measurement scanning systems are known in such applications which can distinguish between received high energy and low energy x-rays. However these systems are limited in their ability to distinguish between different materials which compose a target. Such dual energy systems are in particular limited to assessing whether target material contains an inorganic, organic or metallic materials.

Such existing security scanners provide limited information as a consequence of their limited resolution of energy level. X-ray scanning systems are known for laboratory environments which can resolve a wide number and range of different energy levels for received x-rays. However, these types of laboratory equipment are comparatively expensive to purchase, require a high degree of maintenance and are also complicated to use. Such laboratory type equipment cannot readily be transplanted directly into environments where security based scanning equipment is required, and in particular cannot function in real time to provide results quickly. Generally the detector systems provided in such security x-ray scanners do not readily differentiate the energy levels of received x-rays, but simply indicate the amount of x-ray flux received which has been transmitted through a target at either a high or low energy level.

This characteristic of such dual energy x-ray absorption based detection systems explains why this technology is mostly used only to detect the presence of materials with inorganic compositions. In the case of explosives the compounds in question generally fall within the realms of organic chemistry, where the x-ray absorption characteristics of explosive materials can be very similar to those of other innocuous organic materials. Due to the limited ability of dual energy x-ray absorption systems to distinguish or resolve the energy level of received x-rays transmitted through such target, distinctions cannot easily be made with respect to any particular composition of a target.

This limitation of dual energy x-ray absorption technology also explains why it is not used in other composition determination applications. On-line or real time composition determination has many and varied uses outside of security applications such as, for example, in quality assurance for industrial processes, diagnosis scanning for veterinarian or medical procedures, or any other suitable application where the exact composition of the materials making up a target is not known in advance.

Those skilled in the art should appreciate that the security applications discussed throughout this specification are one obvious use of a target composition determination apparatus, which could be used to rapidly and non-invasively scan a target and determine its composition.

In a number of applications it would be preferable for such composition determination work to be completed in real time, such as for example, when aircraft luggage articles or products on a production line conveyor are moved past or through a scanning apparatus. In such instances it would be preferable to use a fast scanning methodology where the results obtained from the scanning system can be quickly processed to automatically provide a detection indication while the scanned target is still in the vicinity of the scanning system.

For such real time detection systems to operate, it is envisioned that the x-ray emission and detection systems would need to operate with comparatively high through put rates when compared with existing security x-ray scanning technology. In such instances a single band or energy level emission system would need to iterate through multiple energy levels for the same picture of results that would be available when the entire spectra of x-ray energies is transmitted in a single burst emission at one time.

Existing x-ray detection systems can also employ scintillator based detection systems, which convert incoming x-ray radiation to visible light energy, which is subsequently collected and amplified by a photo sensitive component. Such scintillator detectors are vulnerable to statistical uncertainty in the measurements taken, and limited in being able to resolve received x-rays with different but nearby energy levels.

It is known to provide an x-ray scanning system which measures the absorption of x-ray energy by a target across a wide spectrum of x-ray energies to determine potential composition of a target. In particular U.S. Pat. No. 6,950,492 discloses a CT focused medical composition determination system which employs an x-ray generation system to transmit a single energy level or band of x-rays at one time at a target body. Such a system is unsuitable for real time scanning applications in that the iterative, band by band approach disclosed for x-ray emissions would not allow an effective throughput of targets to be scanned in a reasonable time frame.

It would therefore be of advantage to have an improved x-ray absorption based detection system which addressed any or all of the above problems. In particular, it would be of advantage to have an x-ray absorption based detection system which could rapidly scan or investigate targets of interest, be they in security applications, or for quality control reasons in an industrial application for example. Furthermore such an x-ray absorption detection system which could resolve or distinguish between different component materials with similar x-ray absorption characteristics would also be of advantage over prior art. In particular a detection system which could automatically provide a detection indication or transmission specific to a particular material found within a target to trigger a predetermined response would also be of advantage.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a target composition determination apparatus which includes, an x-ray emission element configured to concurrently transmit x-rays with a plurality of different energy levels at a target, and an x-ray detection element configured to receive x-rays which have interacted with the target and to determine the energy levels of each of said received x-rays, said x-ray detection element being configured to generate at least one output signal indicative of the number of x-rays which have interacted with the target and the energy levels determined for each of these x-rays, and a processing element configured to receive said output signal or signals and to indicate the presence of at least one component material within the target using the received detection element signal or signals and a calibration prepared for the target.

According to yet another aspect of the present invention there is provided a target composition determination apparatus substantially as described above wherein the output signal or signals of the x-ray detection element provide x-ray absorption spectrum information for the target.

According to yet another aspect of the present invention there is provided a target composition determination apparatus substantially as described above wherein the target to have its composition determined is luggage or cargo to be carried on a vehicle.

According to a further aspect of the present invention there is provided a target composition determination apparatus substantially as described above wherein the processing element uses a multivariate calibration prepared for the target.

According to yet another aspect of the present invention there is provided a target composition determination apparatus substantially as described above wherein a multivariate calibration is prepared using specific component materials of interest against an unknown background of component materials.

The present invention is configured to provide a target composition determination apparatus as well as a methodology for determining the composition of a target. Preferably the present invention may be optimised or implemented so as to allow for target composition processes to be completed in real time on a line, array or flow of target articles. However in other instances, composition of targets may be determined individually or batch processed in non-real time.

Preferably the component materials to be identified and have their presence determined may be known compounds, compositions or materials, with their type being determined by the application in which the present invention is employed. Such component materials to be identified or have their presence determined may also include unknown compounds, materials or compositions, the presence of which are not expected within a target. Such unknown materials may therefore form a component material of interest in conjunction with the present invention.

Preferably the present invention may be used to distinguish between different types of compounds which have similar energy absorption characteristics for the x-ray band of electromagnetic energies. As discussed above, x-rays have strong penetrating powers and the capability to penetrate the entire volume of a target.

In a further preferred embodiment the present invention may also be configured or adapted so as to allow different types of organic compounds with similar x-ray absorption characteristics to be differentiated from one another when present within a target. Prior art security based x-ray absorption scanning systems have difficulty differentiating such materials from one another.

In a further preferred embodiment the present invention may also identify the volumes, weights, dimensions or amounts of component materials of interest.

In a preferred embodiment a target to have its composition determined may be luggage or cargo to be loaded onto a vehicle. In a further preferred embodiment the targets to be investigated using the present invention may be the luggage of aircraft passengers, and potentially the aircraft passengers themselves. In such instances the present invention may preferably be adapted to focus on a stream or line of luggage (or possibly passengers) and to scan these targets consecutively in real time to detect the presence of security threats or contraband.

Reference in general throughout this specification will be made to the present invention being used as a real time security scanning system for aircraft luggage. However, those skilled in the art should appreciate that the present invention may investigate the composition of other types of targets and it should not be considered as only being useful in security based applications.

For example, those skilled in the art should appreciate that other types of targets such as (for example) milk flows within conduits in a dairy shed, letters or other forms of postal type mail, or manufactured products present on a production line conveyor belt may be investigated for the presence of contaminants and/or variations in compositions. Those skilled in the art should appreciate that a range of biological materials may also form a target, including (for example) cheese or meat carcasses.

Alternatively, the present invention can be used to scan live targets such as animals or human bodies in veterinarian or medical diagnosis applications to identify the presence of harmful compounds.

Furthermore, the present invention may also be employed within computer assisted tomographic scanning (CAT) operations which take measurements of x-ray absorption through more than one plane of a target to be scanned. Those skilled in the art should appreciate that a wide range of applications are available for the present invention ranging from a single plane to multi-planar applications.

Preferably the composition determination apparatus provided includes at least one x-ray emission element. An x-ray emission element can be used to concurrently transmit x-rays with a number of different energy levels towards a target.

In a preferred embodiment an x-ray emission element employed by the present invention may use any number of x-ray generation techniques modelled on the Coolidge tube. These Coolidge tube type emitters can be excited to produce x-ray radiation, potentially which spans the entire spectrum of x-ray radiation energies available.

In general terms reference throughout this specification will also be made to an emitted x-ray having a particular "energy level". Those skilled in the art should appreciate that this reference to the energy level of an x-ray encompasses the resolution of the measuring equipment used and its margin of error, so that a particular defined energy level for an x-ray may encompass actual x-ray energies close to but not directly at the specified energy of that particular level. Energy levels of x-rays as referenced throughout this specification should therefore not be considered as absolute values but instead a range of values in proximity to a specific energy level.

The present invention is configured to collate an x-ray spectrum for a target scanned with x-ray radiation where all x-rays received by an x-ray detection element which have interacted with a target have their energy levels determined individually. Preferably the energy levels determined for each x-ray photon received can be divided into a number of essentially distinct or substantially non-overlapping energy bands. Those skilled in the art should appreciate that due to engineering limitations there may be some minimal overlap between adjacent energy levels capable of assignment to a particular photon where this overlap is to be minimised in practice where possible.

In some alternative embodiments specific sections or selections of the x-ray energy spectrum may be selected for transmission at a target. These portions of the spectrum may be selected for particular types of targets to capture the most variability in the absorption spectrum information available, and hence allow the composition of the target involved to be determined accurately. Furthermore by selecting portions of the x-ray spectrum, well known response phenomenon such as K-line transitions may be avoided or deliberately included in the absorption information to be employed.

In further alternative embodiments the output of the x-ray emission element may be filtered prior to the x-rays it generates reaching a target to be scanned. In such embodiments the above techniques may be employed to investigate only particular energy bands of the x-ray spectrum available.

However, in a preferred embodiment the x-ray emission element may be used which is to be energised, operated or configured to emit x-ray radiation which spans the entire spectrum of energy levels available. For example, in a preferred embodiment an x-ray generation material may be bombarded with a stream of electrons to induce the emission of x-rays to be directed towards a target under investigation. The entire spectrum of all x-ray energies available can be present with transmitted x-rays subsequently being received with a detection element on the other side of the target. In such instances x-rays may be transmitted with a detection element potentially selecting for assessment particular areas of the entire x-ray spectrum which are of interest.

Preferably the x-ray emission element employed may be used to concurrently transmit x-rays with a plurality of different energy levels at a target at any one time during a single operation or actuation of the x-ray emission element.

In a further preferred embodiment the emission element may be employed to continuously transmit a stream of x-rays towards a target, or a region where a target is anticipated to be at some future time. However, in other embodiments the actuation or triggering of the emission element may be completed through a proximity sensor which determines when a target is moved into a region into which the x-rays generated are transmitted.

Reference in general throughout this specification will be made to the x-ray emission element employed transmitting a continuous stream of x-rays which span substantially the entire range of energies levels available within the x-ray spectrum. However, those skilled in the art should appreciate that a stream of x-rays need not necessarily be emitted, as pulses of x-rays or alternatively the periodic actuation or operation of an x-ray emission element may also be employed in conjunction with the present invention.

Those skilled in the art should also appreciate that references to the use of a single transmission plane for x-ray photons throughout this specification should in no way be seen as limiting. Those skilled in the art should appreciate that the emission element or elements employed may also be arranged or configured to transmit x-ray photons over a plurality of transmission planes if required by the application in which the invention is employed.

Preferably the apparatus provided may also include an x-ray detection element. This detection element may receive x-ray photons which have interacted with a target and have not been absorbed by the target. Such an x-ray detection element may both receive incoming transmitted x-rays and also determine the energy levels of these received x-rays. The detection element employed may determine or assign one specific energy level value to each x-ray photon it receives. The detection element may therefore resolve the energies of individual x-rays on a photon by photon basis with the energy levels determined being one of a range of substantially non-overlapping or discrete energy bands or levels.

In a preferred embodiment the x-ray detection element may include appropriate supporting circuitry or components which allow for the individual energies of discrete x-ray photons to be resolved. For example, in preferred embodiments the x-ray detection element may include or have associated with it a multi-channel analyser (MCA) which can be used with signals generated by a transducer or transducers exposed to incident x-ray photons. Such MCA components can readily cope with large numbers of relatively high speed signals and therefore can be employed to individually resolve the energies of each x-ray photon incident with the detection element.

X-ray photons which have interacted with a target may be subsequently detected by an x-ray detection element. Such interactions may include a range of processes from a straight forward transmission of x-ray photons through a target, through to forward or potentially back scattering of x-rays by a target. Those skilled in the art should appreciate that a range of such different types of interactions may be used to derive x-ray spectra information from which a target composition assessments may be made.

Reference in general throughout this specification will however be made to an x-ray detection element being employed to collect or collate x-ray absorption spectra for a target. Such absorption spectra can be collated from x-ray photons which have been transmitted directly through a target without deviation, and hence an absorption spectra may be determined by a subtraction of an empty field state from a field containing a target. However, those skilled in the art should appreciate that other interaction processes such as forward or back scattering of x-ray photons may also be measured by an x-ray detection element and employed in conjunction with the present invention if required. References to x-ray absorption spectra used throughout this specification should in no way be seen as limiting.

In one embodiment the detection element may consist of a range or array of individual detection components, with each component being configured to detect x-rays with a specific energy level, or within a band of energy values. In such embodiments each detection component may resolve the x-ray flux transmitted through a target for a particular band of energies. In this case each detection component may be able to resolve x-ray energy to a specific degree of accuracy, with each detection component thereby being able to indicate it has received an x-ray with an energy level within its particular band of energies. The energy measurement resolution of such detection elements may be tailored to the specific application within which the present invention is used, and in particular the cost of the apparatus to be provided.

However in a preferred embodiment the detection element provided may be sensitive to receive x-rays across the majority of, or at least a substantial part of the x-ray spectrum. In such embodiments banks of such detection transducers may form a detection element to receive x-rays transmitted through a target along a number of different paths through the target. Preferably therefore a single detector element may be composed from a plurality of detector transducers which form an array to receive x-rays.

Those skilled in the art should also appreciate that the x-ray detection element employed need not be sensitive to the entire spectrum of x-ray energy available. For example in some instances specific portions or sections of the entire x-ray spectra may be selected due to the high variability in a targets response to these particular energies. Detector systems which are sensitive to these portions or sections of the x-ray energy spectrum therefore only need to be provided.

Those skilled in the art should appreciate that the x-ray spectra information employed in conjunction with the present invention need not necessarily be continuous across the entire spectra but could be composed of selected portions of the spectra of use in distinguishing between component materials with a similar x-ray absorption response.

Preferably the x-ray detection element provided may generate at least one output signal which indicates x-ray energy and associated x-ray fluxes for these energy levels. In a further preferred embodiment where a detection component is provided for each band of x-ray energies to be considered, the detection element may generate an output signal for each detection component and hence each specific energy level step to be resolved. This combination of output signals may then provide x-ray absorption spectrum information to be used to determine a composition of a target.

In a preferred embodiment an output signal from the x-ray detector element may be composed of the response of the detector transducer or transducers organised in terms of a continuous array of sequential consecutive time periods. In such embodiments the responses of a transducer may be batched together over a pre-selected time period which defines a collection rate and the resulting physical resolution of the invention when a target is moved relative to the detector element. In such embodiments consecutive blocks of time may be associated with detector element results or responses, with the length of the time periods or the resolution of the system being determined by both the desired physical resolution for the application of the invention and also the speed at which targets move relative to the apparatus provided.

In such instances, the detection element may be configured to receive and determine the energy levels of sufficient numbers of photons per second to maintain both the required spatial resolution along the axis of movement of a target and sufficient accuracy of composition measurement. Spatial resolution is a function of the speed of the target through the invention, the detector element geometry and the time required to collect sufficient photons for the determination of the target's composition. The time required to collect sufficient photons depends on the x-ray flux through the detector element, which is determined by the characteristics of the target, the x-ray source and detector element geometry, and the rate of photon emission from the x-ray source.

In a preferred embodiment an x-ray detection element may be formed from any transducer or collection of transducers which are capable of discriminating the energies of x-ray photons.

In one alternative embodiment of the present invention, an x-ray detection element may be formed from a single transducer which may receive and discriminate energies of photons which have traveled over a number of different transmission paths. In such embodiments this single transducer may cover or span an area of interest adjacent to a target being scanned. For example, in one such embodiment an x-ray detection element may be formed by a single scintillator based system configured to receive x-ray photons over an area of interest as discussed above.

However, in a preferred embodiment a detection element may consist of an array of individual detection components, with each component being configured to detect x-rays within a band of substantially non-overlapping energy values.

In a further preferred embodiment the x-ray detection element may employ an array of photodiodes to convert received x-ray photons to an electrical output signal or signals. Photodiodes are a preferred form of component to employ as they provide a direct measurement of x-ray energy received in a resulting electrical output signal. In real time scanning applications particular types of photodiodes may readily deal with high photon fluxes and provide clear energy level resolution. This may be contrasted with scintillator based detector systems which as a consequence to their operation have a level of statistical noise or error present in their results and also do not readily resolve nearby energy levels.

In some embodiments the x-ray detection element may be implemented through an array of cadmium telluride (CdTe) or cadmium zinc telluride (CdZnTe) photodiodes. These photodiodes have a relatively fast response to incident x-ray photons and are capable of capturing x-ray photons to relatively high energy levels.

In other embodiments the x-ray detection element provided may include an array of gallium arsenide (GaAs) photodiodes. Gallium arsenide photodiodes can be configured to have a very fast response to incident x-ray photons and are also capable of capturing x-ray photons to relatively high energy levels.

Those skilled should appreciate that the above types of photo diodes may be employed to assist in the resolution of signals sourced from photons with similar or close energy levels, preferably through the provision of a post processing system which receives signals from the detector element provided.

Those skilled in the art should also appreciate that a range of other types of photodiodes may also be employed in conjunction with the present invention depending on specific application in which it is employed.

According to a further aspect of the present invention there is provided a method of data processing that leads to the issue of an alarm indicator in response to the detection of at least one material of interest within a target scanned by x-ray radiation.

According to a further aspect of the present invention there is provided a method of issuing an alarm indicator in response to the detection of at least one material of interest within a target scanned by x-ray radiation, said method being characterised by the steps of;
  i) receiving at least one input signal from a detection element, said input signal or signals indicating the numbers of x-ray photons which have interacted with the target and the energy levels determined for each of said x-ray photons, and
  ii) processing said at least one input signal to predict the presence of at least one material of interest, and
  iii) if a prediction of the presence of at least one material of interest is made, issuing an alarm indicator.

According to a further aspect of the present invention there is provided a method of issuing an alarm indicator in response to the detection of at least one material of interest within a target scanned by x-ray radiation, said method being characterised by the steps of;
  (i) receiving at least one output signal from a detection element, and
  (ii) standardising said at least one output signal, and
  (iii) preparing an image of at least a portion of the target scanned, wherein each pixel of said image includes information as to the predicted presence of at least one material of interest within the target,
  (iv) validating the predicted presence of at least one material for a pixel by comparing said pixel with other adjacent pixels of the image prepared, and
  (v) issuing an alarm indicator when a valid prediction of the presence of at least one material of interest is made.

According to a further aspect of the present invention there is provided a method of issuing an alarm indicator substantially as described above, wherein said predicted presence information associated with at least one material of interest is prepared using a calibration particular to each material of interest to be detected.

According to a further aspect of the present invention there is provided a method of issuing an alarm indicator substantially as described above wherein predicted presence information is prepared using a multivariate calibration, said multivariate calibration being particular to a material of interest to be detected.

In a preferred embodiment the target composition determination apparatus may also include a processing element. Such a processing element may receive the output signal or signals of the detection element as an input.

In a preferred embodiment the processing element may be formed by at least one microprocessor, or an array of microprocessors, which have ancillary support systems such as memory, hard disks and so forth. In a further preferred embodiment the microprocessor or processors provided may be located within the same collection of equipment used to provide the x-ray emission element and detection element. However, in other embodiments a distributed processing system may be used where the processing element may be located at a remote location but be in communication with the detection element if required.

In a preferred embodiment the processing unit may receive the output signals from the x-ray detector and collate same to provide an initial assessment of the number of x-ray photons transmitted through a target during a predefined time periods, and the energy levels of these x-rays. In a further preferred embodiment the processing element may include or be associated with enough memory to allow the resulting signals from the detector to be stored from a plurality of such time periods. This storage facility can allow a whole picture or image of an entire target to be built up over time as the target is conveyed past the detector over time.

In such instances the predefined time periods associated with a detector signal may collate or provide all the data to be presented within a pixel of an image of an entire target. In such embodiments a target may move relative to the apparatus provided, with points on the surface of the target being illuminated by x-rays once only as the target moves through or passed the apparatus. The time periods or division associated with the detector element signals will therefore combine with the speed of target movement to set the physical resolution of the system and hence the amount of data present with respect to a particular pixel representing a point or small region on the surface of a target being scanned.

Such a processing element may be employed to implement the issuing of an alarm indicator in response to the detection of at least one material of interest within a target scanned by x-ray radiation. This processing element may initially receive at least one output signal from a detector element and then subsequently process said output signal or signals to predict the presence of at least material of interest. If the processing element does predict that at least one material of interest is present it can subsequently issue an alarm indicator.

Those skilled in the art should appreciate that the processing element may execute a number of different individual processes to predict the presence of at least one material of interest, with the form, arrangement or collaboration of these processes being dictated by the individual application and implementation of the present invention in a number of embodiments. For example, in some basic applications this processing phase may employ the use of calibrations in isolation to detect the presence of at least one material of interest. In other embodiments additional processes, such as a prior signal standardisation process, or a subsequent image processing validation and/or pattern detection process may also be run in conjunction with the use of a calibration. Those skilled in the art should appreciate that some variability in implementation is envisioned in conjunction with the processing of input signals.

In one embodiment the processing element may be employed to implement a standardisation of resulting output signals from the detector element. This standardisation process may employ x-ray wavelength standards to map the result signals from the detector to specific known x-ray energy levels. Furthermore, the processing element may in this role normalise or standardise the resulting signals from the detector to ensure reproducibility of results for the given device and for this device in comparison to other nominally identical devices employed elsewhere, both in the short term between individual pulses of x-rays being generated, and the long term over use of the invention with many different targets.

Those skilled in the art should appreciate that components used to provide the apparatus of the present invention may be susceptible to noise or error. For example, amplifiers of electrical signals or analogue to digital signal conversion elements may be susceptible to signal distortion problems in addition to drift. For example environmental factors, such as temperature, received levels of photon flux or age of the components themselves may cause such problems. Furthermore the response profile of such components may not necessarily be linear in nature. The use of x-ray wavelength standards can allow known x-ray spectral features to be identified in the response of the signals of the system and therefore allow the current response of the apparatus provided to be modelled and potentially linearised. Scanning such standards periodically will allow for such sources of noise or error to be accounted for and removed.

In a further embodiment wavelength standards may be employed which provide at least two uniquely known features in the recorded energy spectrum. Ideally, at least two features should be near the upper and lower bounds of the spectrum, and additional features should appear at known and more or less regular intervals in between the upper and lower bounds. Taken together, these features may provide a wavelength standard or set of standards.

Reference standards comprising materials with known x-ray spectral characteristics but constructed of materials capable of withstanding repeated scanning without affecting their x-ray spectra may be employed, depending on the particular requirements of the eventual application for the device. Considerations of the environment of use (such as a highly acidic atmosphere for example) may mean materials suitable for wavelength standard, for example copper, would not be suitable for long-term, regular scanning as reference standards.

Such reference standards can be inserted into the x-ray beam immediately before a target to be scanned and optionally immediately afterward. In continuous flow applications reference standards could be inserted at intervals during scanning, and any identified altered attenuation compensated for during processing of the absorption spectrum. The x-ray generator output and specific detector responses could therefore be monitored at all times to provide continuous feedback to a baseline restoration system.

Materials that can conveniently be used to create Wavelength Standards could include:
  Radio-nuclides of various types as appropriate for the detector in use
  Filters made from heavy metals and alloys of metals such as copper, tin, gold and silver, and other heavier metals which exhibit k-edges and other sharp features when irradiated by a broad spectrum source such as an x-ray generator.
  The radiation peaks from the target of an x-ray generator, such as a tungsten-target generator.

These features are sharply defined in the resultant spectrum. As the energies are defined by the fundamental characteristics of the elements or transitions concerned, they are invariant and provide convenient and highly stable points to calibrate the energy axis against.

For example, choosing wavelength standards made of molybdenum, tin, cerium, gadolinium, gold and lead, and using a tungsten target x-ray generator gives a good spread of features across the spectrum from 13 keV to 88 keV.

Further improvement may be gained also in some embodiments by characterising the differential non-linearity of any analogue to digital converter (ADC) used, for example by applying a linear ramp or triangle wave to the ADC and analysing a histogram of the output.

Materials that can conveniently be used to create Reference Standards could include the above, but also:
  Materials with no particular sharp x-ray spectral features, but with good physical and x-ray stability, such as Teflon, Aluminium, etc, or
  Materials that may lend themselves to manufacturing requirements to create the desired mechanism to insert and remove the Reference Standard as required in the beam path Reference in general throughout this specification will also be made to a processing element performing a standardization process with respect to received detection element output signals substantially as described above. However those skilled in the art should appreciate that in other embodiments such a standardization process may not necessarily be run and should not be considered essential in the implementation of the present invention.

Preferably the processing element may be programmed with appropriate instructions to apply input absorption spectrum information to at least one multivariate calibration prepared previously for the target. In such embodiments the processing element may also provide a calibration unit. An operation using a calibration and the input detector element results should therefore yield an indication as to whether a selected or particular compound material is present within a target. In a further preferred embodiment one or more of the multivariate calibrations used may also determine quantitatively the amount, volume, weight or potentially dimensions of a particular component material of interest present within a target.

Reference throughout this specification will also be made to the present invention employing at least one multivariate calibration. However, those skilled in the art should appreciate that other types of calibrations and other techniques may be employed to determine whether a particular material of interest is present within a target in other embodiments.

Furthermore, reference throughout this specification will also be made to a calibration being used to detect the presence of a known component material of interest. However, as discussed above, a component material of interest may alternatively be formed by an unknown component which does not correlate with any calibrations prepared or available for use in combination with the x-ray spectra collected for a target. In such an embodiment the present invention may be employed to isolate the presence of component materials which are not expected to be present within a target.

In one embodiment the present invention may make an assessment as to the contribution of confounding materials which may be present in a target. These confounding materials may have a similar x-ray absorption response to that of the material to be detected within a target. Alternatively, a confounding material may have non-similar x-ray absorption characteristics to the component material of interest for which the calibration is prepared. For example, in an embodiment where non-similar absorption characteristics may be provided by materials which strongly absorbs or blocks x-rays.

In such instances background spectral data may be obtained from scanned objects which are known not to contain the target material to be detected. A spectral data set for a current object under investigation may then have the contribution of a back ground spectral data set in addition to the known response patterns of at least one confounding material subtracted from the scanned spectrum received. This subtraction process may then result in any remaining spectral contribution being attributed to that of the target material to be detected.

Preferably the present invention may employ at least one multivariate calibration prepared for a particular class of targets prior to the composition of such targets needing to be determined. Multivariate analysis procedures consist of a set of statistical data analysis methods which correlate the spectral responses, their variances and co-variances against previously identified material levels, and/or the presence of unknown and/or undesirable material or materials.

One particular type of multivariate analysis, being Principal Component Analysis (PCA), can be used to decompose a data set into a number of uncorrelated or orthogonal variables. This technique can isolate the minimal number of variables which can be used to represent most of the variability present within a data set. These newly defined variables provided through a PCA approach can be in turn used for the purposes of displaying or organising the data set involved.

In addition, as these principal component variables are orthogonal or independent with respect to one another they may be rotated to choose or select the absorption response of one particular component material of interest which is to have its presence detected within a target. When these redefined or selected material variables are used as axis to plot the absorption spectra that is available, the displayed results can provide clear separations between different compounds which may have similar x-ray absorption responses. By selecting a particular target material of interest to derive one of the axis of the results plot required, principal component analysis techniques may be used, for example, to differentiate between organic compounds with similar x-ray absorption responses.

In some embodiments, this rotated PCA analysis may be used in conjunction with clustering analysis techniques (for example SIMCA or KNN) to identify materials of known or unknown composition, relative to the particular material axes chosen, hence identify presence or absence of considered materials.

In some embodiments such principal component analysis techniques may in turn be extended to provide a principal component regression (PCR) calibration. In such instances the principal components may be determined for the x-ray absorption data set involved, and one particular component material of interest may be selected to define one of the axis or principal components to be used. Once the principal components have been isolated a regression procedure may then be completed to provide a calibration to be used in conjunction with incoming measurement data from the x-ray detection element.

However, in a preferred embodiment a multivariate calibration may be prepared using a Partial Least Squares (PLS) regression. A PLS regression calibration employs a similar approach to principal component analysis. However, the PCA and subsequent PCR approach is most effective in instances where the distribution of measurements present within the calibration data set is relatively consistent across the entire data set. A PCR calibration can therefore be prepared based on the variability introduced by individual components. Conversely, in instances where there is a significant degree of variability across the calibration data set, a PLS regression may be employed. A PLS regression also introduces the variability present within the results of the calibration data set in the assessments of the principal components to be defined for the resulting calibration. The principal components ultimately defined using a PLS technique will therefore also take into account the variability present within the calibration data set and model same.

A PLS regression calibration can provide the present invention with significant advantages when there is uncertainty present with respect to the components which could be present within a target. The use of an appropriate set of test targets in the preparation of a calibration data set can go some way to mitigating problems present in applications such as this including, for example, security scanning of luggage or cargo. The multivariate calibration prepared earlier for such test target sets can be used to isolate at least one particular component of interest such as contraband or explosive compounds, and to resolve this compounds response in the captured x-ray absorption spectrum from a scanned target.

In some embodiments, the data sets collected (perhaps over long time frames) may be diverse and sufficiently structured as to make non-linear correlative techniques feasible, such as neural networks (NN). Multivariate calibrations based on NN may potentially identify material presence and/or material levels within a target in either a highly variable environment (for example airline luggage) or a more controlled environment (for example a production line).

Furthermore, as discussed above those skilled in the art should appreciate that other techniques for detecting the presence of a material of interest may be used instead of or in addition to multivariate calibrations. Furthermore, neural networks may be employed in such instances to provide improvements in the overall accuracy of the resulting system—irrespective of whether multivariate calibrations or any other type calibrations are employed.

In all multivariate analyses, there are a wide number of pre-processing spectral techniques that may be employed. These can include, but are not limited to:

Extended multiplicative signal correction (EMSC) methods;

Standardised Normal Variate (SNV) to remove or enhance scattering;

Derivatives to remove or enhance baseline drifts and/or axial tilts and so forth;

Optimised Wavelength selection, to only employ sections of the spectra that enhance the detection ability;

Orthogonal Signal Correction, to correct for (or enhance) some forms of cross-correlation between spectral groups.

Any multivariate calibration may employ any or a number of such techniques to enhance desirable features relevant to the particular property or material being predicted.

In a preferred embodiment the calibration unit functionality provided may access or use a plurality of calibrations. Each of the calibrations used may be configured so as to predict the presence of a particular component material of interest, such as for example, an organic explosive or malignant tumour. A number of individual calibrations may therefore be run by the calibration functionality for each path x-rays traverse through a target. The resulting detector element signals can therefore be employed to provide a series of images of a portion, or preferably the whole body of a target, where each pixel of each image provides information as to the presence of component materials of interest. Such a Result Hypercube can therefore indicate at each pixel which of these component materials has been detected as present.

In a preferred embodiment the x-ray spectrum from each pixel of a target may also be compiled into a hypercube for treating as a single entity, perhaps for subsequent analysis, saving, or directly analysing.

Furthermore, in other applications where the present invention is used in conjunction with multi-planar scanning methodologies (such as CT Scanning), individual image slices may be compiled together to provide tomographic imagery which gives composition detection information.

Reference in general will be made to the present invention employing images and in particular hypercube images throughout this specification. Those skilled in the art should appreciate that such references to images need not necessarily require the display or presentation of graphics to an observer. Such images can be resident in or formed by the collection and organisation of pertinent information in some form of storage media, such as for example, a hard drive or other memory storage components of a computer system. The present invention need not necessarily require the actual physical display of images to be implemented, and those skilled in the art should appreciate that the spectral representation of a target or at least a portion of a target may be used in general by the present invention.

In a preferred embodiment at least one of the image planes of the Result Hypercube may indicated the predicted mass of each component material of interest. In a further preferred embodiment a further such plane of the Result Hypercube may represent a probability estimate for the accuracy of the mass predicted. This information can therefore be used to assess whether a component material of interest is actually present along the transmission path through a target which is associated with a pixel.

In some embodiments the present invention may also include an image processing unit. For example, in such embodiments image processing facilities may be provided through executable instructions run by the processing element. Such an image processing unit may assess either the x-ray spectrum hypercube or the Result Hypercube of a target. This image processing facility may compare adjacent or nearby pixels of the basic image to improve predictions as to whether a deposit of a material of interest is present within a target.

For example, in security scanning applications semtex may be secreted around the lining of a suitcase. Depending on the angle of inclination of which the suitcase is scanned, a clear image may be presented of adjacent pixels predicting the semtex sheet indicating there is a high probability of a large mass of semtex being present with respect to each pixel. In such instances the spatial relationship between adjacent or nearby pixels can be used to validate the composition predictions made, and isolate specific areas of the target where a deposit of material of interest is located.

In a further preferred embodiment an image processing unit may also complete a pattern detection process. For example, in such embodiments the imaging processing unit may look for or detect specific known shapes or articles which may present within a target, such as for example fire arms or weapons. In such embodiments the image processing unit may harness both pattern recognition algorithms in combination with composition determination data to assess whether an article of interest is present within a target.

However those skilled in the art should appreciate that such an imaging processing unit may not necessarily be considered essential to the present invention. Those skilled in the art should appreciate that the Result Hypercube derived as discussed above may readily be employed to provide an immediate prediction or detection of the presence of at least one component material of interest. The provision of an image processing unit may in some instances improve the accuracy of such predictions or the ultimate usability of the system provided in a number of applications.

In a preferred embodiment the present invention may also incorporate an automatic indication alarm system. Such an alarm system may be supplied with the results of the processing unit or a specific image processing unit when it is clear that the system has detected the presence of a mass or deposit of a material of interest. Such an alarm unit may issue an alarm indicator and/or to trigger a number of different actions depending on the particular application which the present invention is to be used.

For example, in one preferred embodiment the results of the system may be displayed graphically to a user with colour, texture, sound or movement in the graphical display presented indicating that a material of interest has been found in a scanned target. Furthermore in other embodiments additional automated functionality may be triggered through such an alarm system. For example, lock systems or audio alarms may be triggered in other embodiments by such functionality.

The present invention may provide many potential advantages over prior art composition determination systems.

The present invention may rapidly and accurately assess whether one or more materials of interest are present within a target in a non-invasive process. Appropriate x-ray emission and detection systems may be used to capture x-ray absorption spectrum information for a target to determine the composition of the target.

The present invention may be used to determine target compositions where there is some variability present with respect to other types of materials or components present within the target. In the case of security scanning systems for luggage or passengers there can be a significant degree of variability with respect to the content of luggage and hence the techniques of the present invention may be optimised to cope with such variable unknowns.

The present invention may also be employed to consider x-ray absorption spectra information to distinguish between different organic compounds which have comparatively similar x-ray absorption characteristics. Through focusing on the useful variable sections of the x-ray spectra available for a target such organic compounds may be readily differentiated from one another. Such differentiation may be completed either through the use of multivariate calibrations or any other relevant applicable calibration generation technique.

The present invention may be configured for use in basic security scanning operations where a target material (such as an article of luggage) is conveyed through or past the invention. In such applications measurements may be made through a single plane of the target to provide imaging data used to assess the likely presence of the masses of particular component materials of interest.

Furthermore, the present invention may also be configured for use in CT x-ray scanning applications which gather image data from more than one plane of x-ray transmissions through a target. The x-ray emission and detection systems employed in conjunction with the present invention may be configured for use with CT scanning systems which can either move emitter/detector arrays, or provide multiple sets of emitter and detector arrays positioned around the circumference of an object to be scanned.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1A:
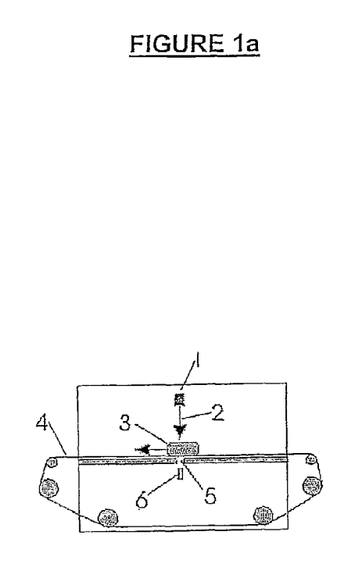
FIGS. 1a, 1b show block schematic diagrams of component elements used to implement a target composition detection apparatus in accordance with one embodiment.
Figure 1B:
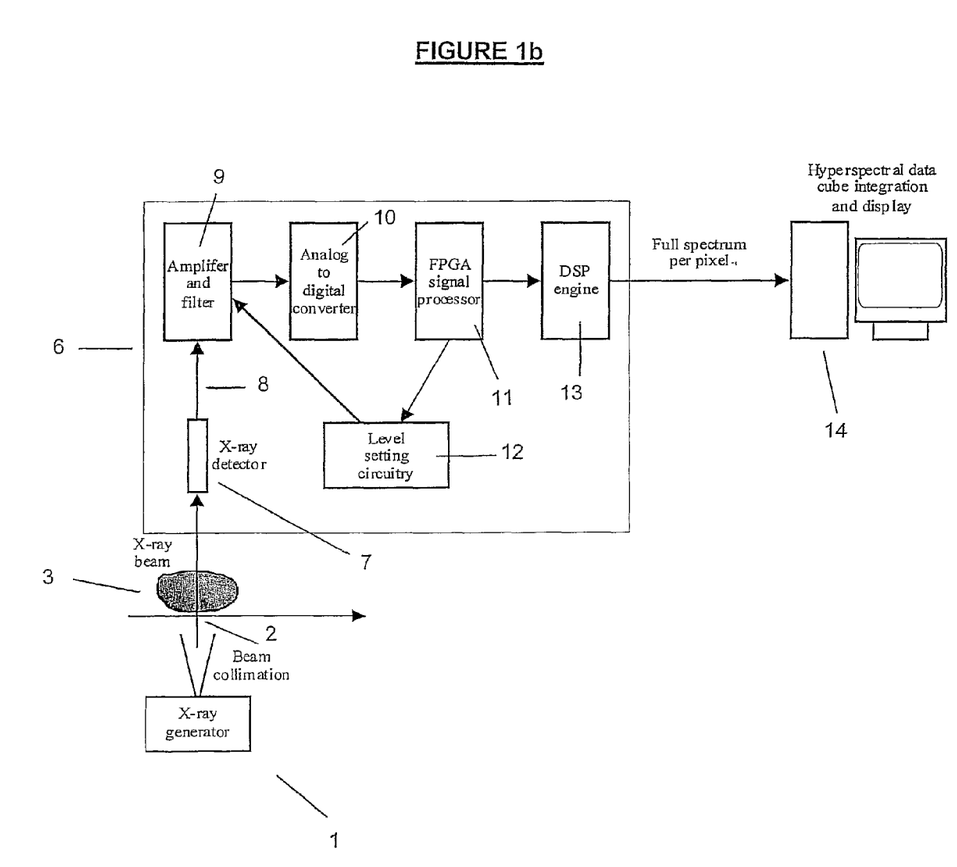

FIGS. 1a and 1b show block schematic diagrams of component elements used to implement a target composition detection apparatus in accordance with one embodiment.

The apparatus shown includes an x-ray emission element (1) which is configured to transmit a stream of x-rays (2) with a plurality of different energy levels at a target (3). The target (3) is supported by a conveyor system (4) used to convey a stream or flow of targets through the apparatus over time. The apparatus shown is configured to operate and scan targets in real time and preferably may be used in a security scanning application.

The x-rays (2) transmitted from the emission element (1) are at least partially absorbed or scattered by the target but some x-ray flux makes it through the target, on to a collimiator (5) and then subsequently to an x-ray detection and processing element (6). These two elements are shown in further detail with respect to FIG. 1b.

FIG. 1b shows an x-ray detection element (7) which is configured to receive x-rays transmitted through the target (3). The x-ray detection element (7) is used to determine the energy levels of the x-rays it receives and to generate a number of output signals which indicate both the number of x-ray photons which are received in addition to the energy levels of these x-rays.

The x-ray detection element (7) is formed from an array or line of individual photodiode components with each being designed to register the transmission of x-rays across a wide band of x-ray energies.

Output signals (8) of the x-ray detection element (7) are subsequently supplied to a pre-amplification and filtering stage (9) and then converted into digital format by an analogue digital converter or ADC (10) in the MCA.

The digital signals generated by the ADC (10) are supplied to a field programmable gate array (FPGA) (11) and a microprocessor forming a digital signal processing (DSP) engine (13). The FPGA (11) and DSP (13) compose a processing element which is used to indicate the presence of at least one component material within the target (3). The FPGA (11) is also linked to level sensing circuitry (13) which provides a feedback loop through to the amplification stage (9) to adjust the amplification and offset levels applied to the original raw analogue signals from the x-ray detection element (7).

In the embodiment shown with respect to FIGS. 1a and 1b, the FPGA (11) is used to analyse the incoming digitised data and prepare an output histogram data structure to be supplied to the DSP engine (13). This histogram indicates x-ray flux per energy level of interest for a particular time period during the scanning operation.

The DSP engine (13) performs the actual operations required on the input absorption spectra information formed by the FPGA's histogram data structure to indicate whether a particular type of component material is present within the target (3).

The DSP engine (13) uses a multivariate calibration in combination with the input spectral information it receives to make this determination. Calibrations are prepared earlier for the particular class of targets under investigation and for specific component materials of interest. The DSP uses a calibration and the input flux intensity values for each energy level to make a determination as to both whether a particular component material of interest (such as for example contraband or explosives) is present within the target (3).

Those skilled in the art should appreciate that in other embodiments multivariate calibrations may not necessarily be employed. For example, in other instances a scanned object spectra may be dissected to remove the effect of background materials in combination with the response patterns of confounding materials to result in a contribution sourced only from a target material to be detected.

The DSP engine (13) is also linked to a display system (14) which can preferably provide a graphical representation of the composition or identity of each component material which is found to be present within the target (3). The DSP engine may also indicate or estimate the quantity of such component materials present within the target (3). The display system (14) may be used to present or display such results in addition (in some embodiments) to providing a graphical image display of the original spectral data received by the DSP (13) from the FPGA (11).

Figure 2:
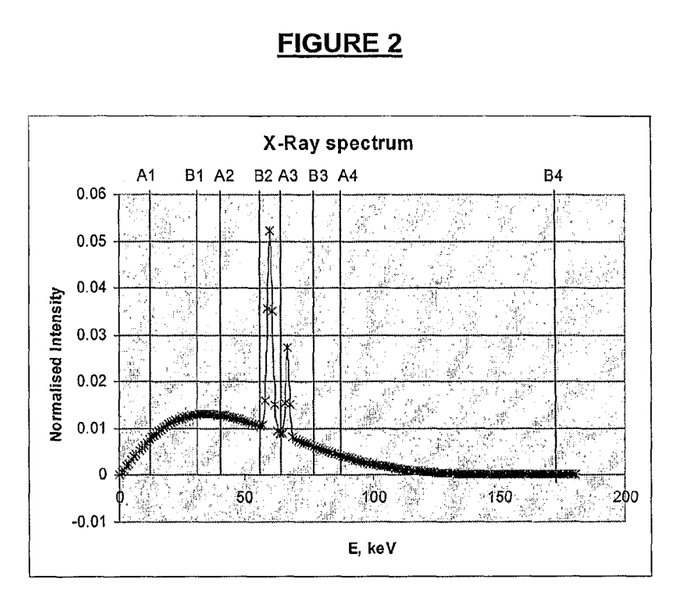
FIG. 2 shows an example graph of an entire x-ray detection spectrum for a target.

FIG. 2 shows an example graph of an entire x-ray detection spectrum for a target.

FIG. 2 clearly illustrates that the high energy spectra available for the target provides very little information and in particular little variation in results. A number of k-band transition emission peaks from a tungsten-target x-ray generator are illustrated at approximately 60 keV.

The bulk of the variability of response of this particular target is present between 0 and 100 keV of the spectrum shown. The present invention may in effect "pick and choose" sections or chunks from the entire spectrum to target areas with high variability (such as between 0 and 30 keV), and also to exclude regions which illustrate non-relevant absorption phenomenon, such as the K-band transitions at approximately 60 keV. This particular optimisation may in turn result in lower data processing loads.

Figure 3:
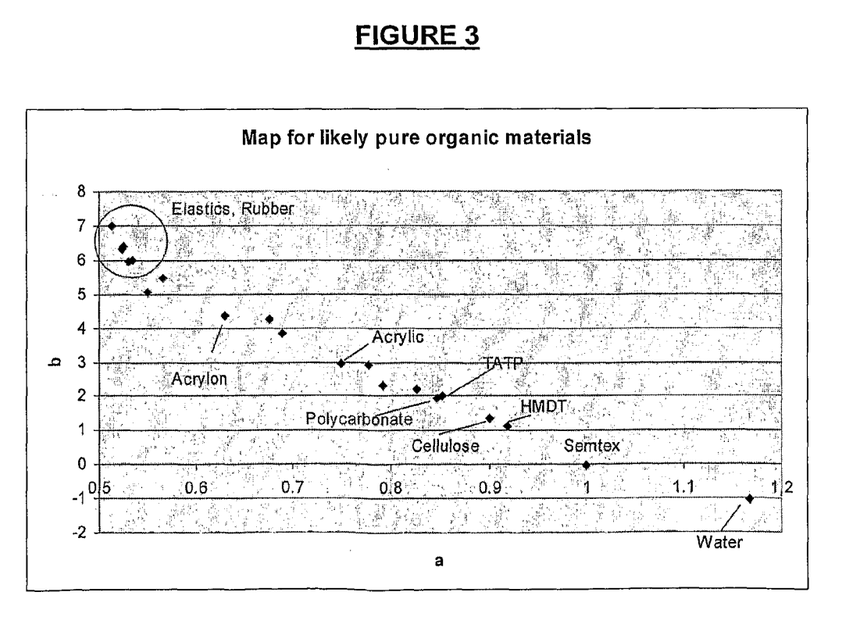
FIG. 3 shows an example plot of component separations which can be made between organic compounds using multivariate analysis techniques and x-ray absorption spectra information.

FIG. 3 shows an example plot of component separations which can be achieved between organic compounds using multivariate analysis techniques and x-ray absorption spectra information.

FIG. 3 illustrates the use of modelled data in a case where the explosive semtex has been selected to define one of the principal components used in such an analysis, and hence the X axis of the plot of component response shown. Principal component analysis techniques can be used to provide such plots preferably to target one particular type of component material of interest. In effect any result from the input absorption spectra information received which appears plotted on the X axis indicates the presence of semtex within the target which has just been scanned.

Figure 4A:
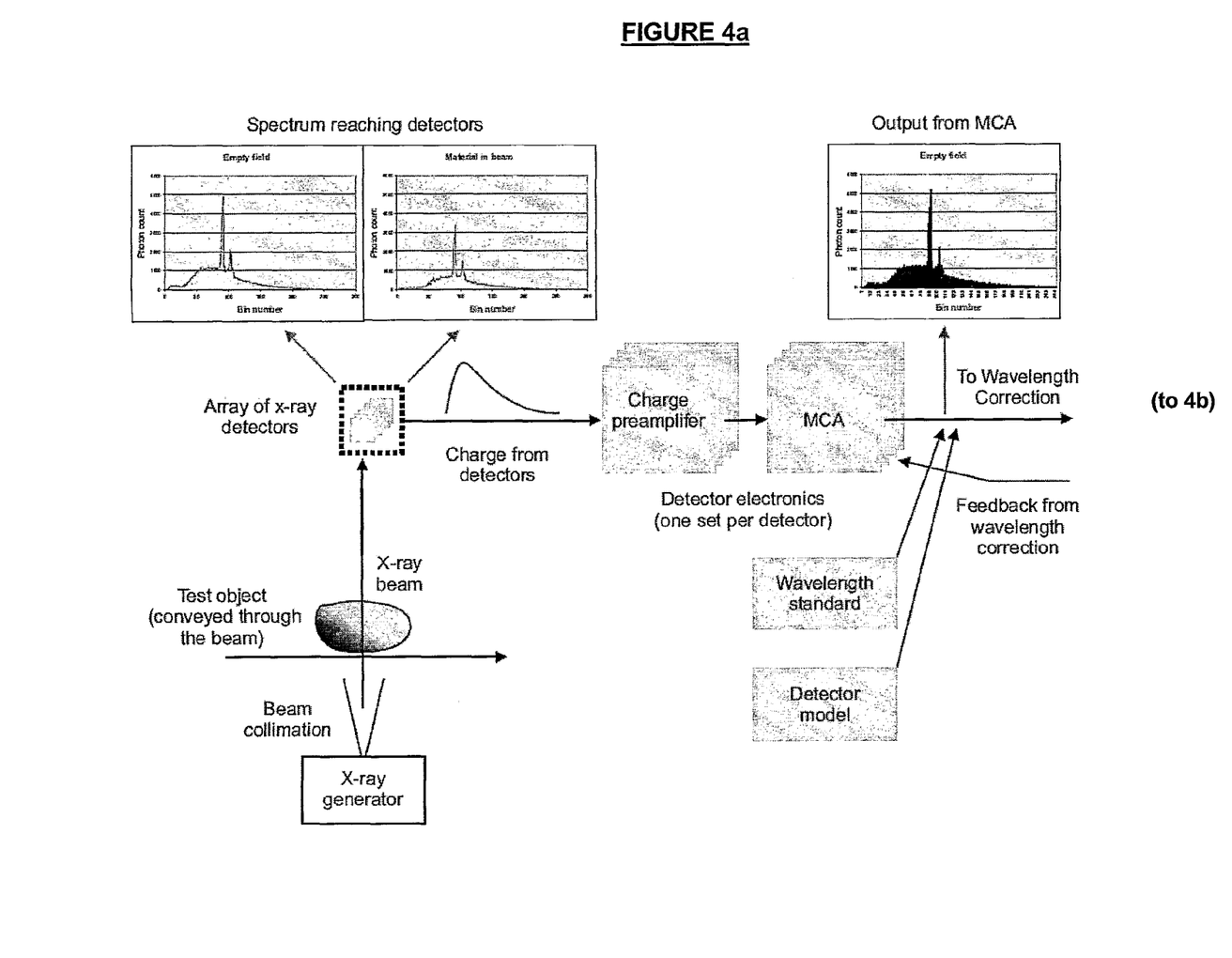
FIGS. 4a, 4b show consecutive flowcharts illustrating data and information handled at various stages through the operation of the present invention in a further embodiment.
Figure 4B:
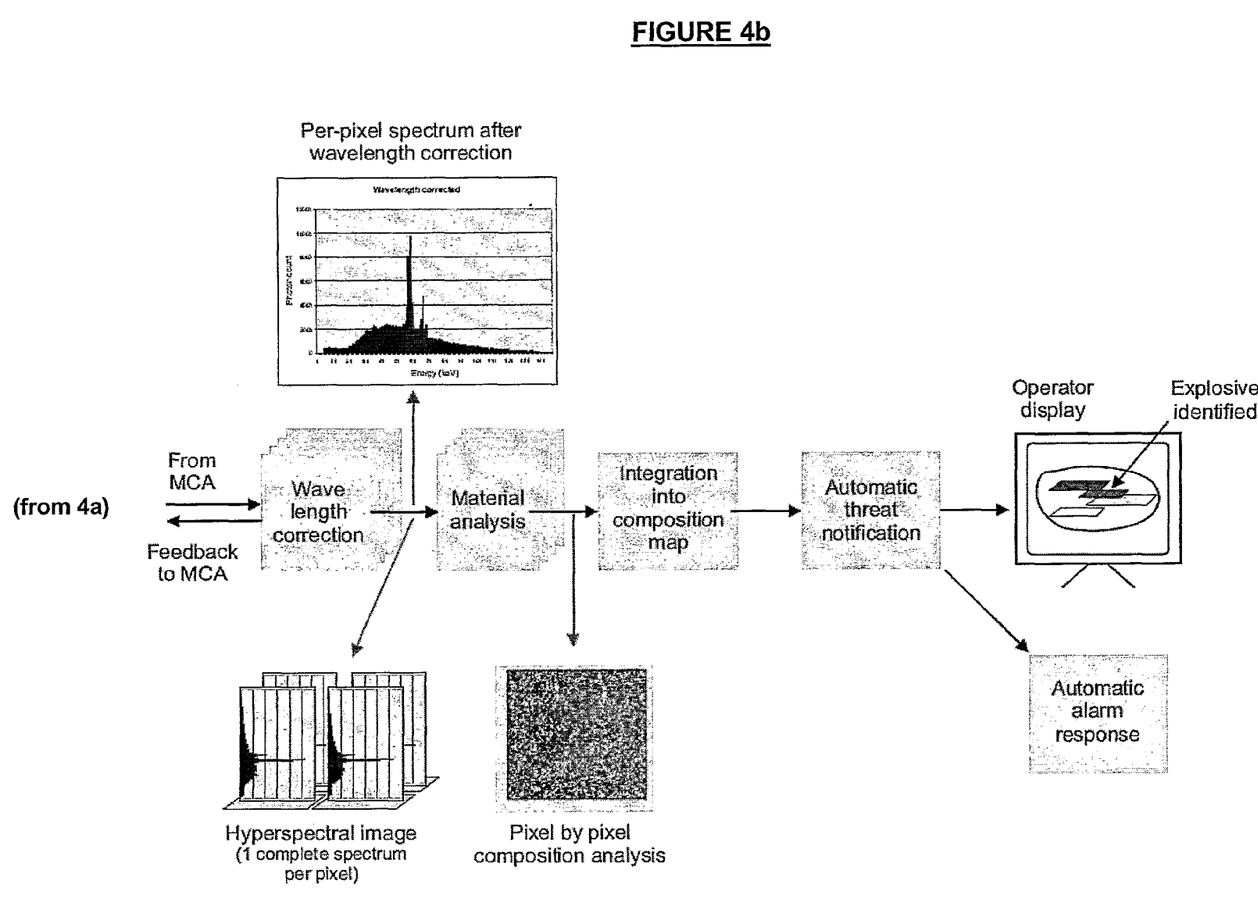

FIGS. 4a and 4b show consecutive flowcharts illustrating data and information handled at various stages through the operation of the present invention in a further embodiment.

FIGS. 4a and 4b show the operation of a similar set of components discussed with respect to FIGS. 1a and 1b, and in particular show further details with respect to image processing and assessment aspects of the invention illustrated in the embodiment shown.

As can be seen from FIG. 4a an array of x-ray detectors are employed to capture x-ray spectrum information. The photon count received from an empty field is substantially higher from that received when a target is within the band or stream of x-rays emitted. An absorption spectrum can be calculated for a target by comparing the empty field spectrum (with no target in the x-ray beam) with the spectrum transmitted through the target when within the beam of x-rays. The difference between an empty field and the non-empty field measurement will therefore provide an absorption spectrum of a target.

These results are collated together by a multi-channel analyser (MCA) where each "bin" is associated with one of a consecutive number of time periods over which x-ray photons are received.

At this stage the detector output signals are standardised through the use of wavelength standards. A model prepared for the detectors can also be used to predict variabilities in detector responses contributed from factors other than the composition of a target being scanned.

A wavelength correction step can also be employed to give feedback to the MCA with respect to detected shifts in the spectrum reported by the detector components. At this stage a baseline restoration process can be completed which can also control amplification applied to the results ultimately provided by the MCA.

Once these output signals have been standardised an image of a target may be compiled with each pixel of the image giving a spectrum of x-ray absorption information. In the embodiment shown a series of image slices or planes can be compiled together by the invention as x-ray absorption data is captured during the traversal of a target passed the array of x-ray detectors. Absorption information from each of these planes or slices through a target may then be compiled to provide an entire image consisting of the number of pixels composited from this overall set of image slices or planes. All the pixels provided will therefore provide a hyper-spectral image of a target represented in terms of x-ray absorption spectrum information.

Next a calibration unit is employed to complete a material analysis phase, providing a Result Hypercube image of a scanned target in terms of predicted composition. Such a Result Hypercube may have a multitude of layers depending on the number of component materials of interest which the original absorption spectrum hypercube is analysed for.

This composition hypercube image is then supplied to an image processing unit which completes a validation of composition detections through a relative image pixel comparison. Adjacent or nearby pixels can have their predicted compositions compared to validate or eliminate same from the results provided by the system. Such validation comparison processes can also include;
thresholding minimum significant size assessment.
2D smoothing processes.
edge detection processes.
sharpness improvement and/or smoothing.
gamma and other non-linear adjustments of the final image prepared.

Once this validation process has been completed automatic threat or alarm notifications can (if required) be generated by an automatic indication alarm system. This system can issue an alarm indicator to trigger an automatic alarm response, such as locking building exits or triggering sirens. This system may also trigger the display of images of the scanned target illustrating the form, shape or position of a component material of interest within a scanned target.

Aspects of the present invention have been described by way of example only and it should be appreciated that modifications and additions may be made thereto without departing from the scope thereof as defined in the appended claims.

What we claim is:

1. A target composition determination apparatus comprising,
an x-ray emission element configured to concurrently transmit x-ray photons with a plurality of different energy levels spanning the x-ray spectrum at a target;
an x-ray detection element configured to receive x-ray photons which have interacted with the target and to determine the energy levels of each of said received x-rays, said x-ray detection element being configured to generate at least one output signal indicative of the number of x-rays which have interacted with the target and the energy levels determined for each of said x-rays, wherein the output signal or signals of the x-ray detection element are batched over a pre-selected time period to define the physical resolution of the target composition apparatus when the target is moved relative to the apparatus; and
a processing element configured to:
receive said output signal or signals;
select output signal or signals having energy levels of greatest significance;
apply at least one multivariate calibration prepared for a particular class of targets to data relating to the number of x-rays which have interacted with the target and the energy levels determined for each of said x-rays as derived from the selected signal or signals, to determine the presence of at least one component material within the target, wherein the multivariate calibration correlates the data, its variances and co-variances against one or more of: previously identified material levels, the presence of an unknown material, or the presence of an undesirable material; and
indicate the presence of at least one component material within the target.

2. A target composition determination apparatus as claimed in claim 1 wherein the target to have its composition determined is luggage or cargo to be carried on a vehicle.

3. A target composition determination apparatus as claimed in claim 1 which also determines volumes, dimensions and/or weights of component materials present within the target.

4. A target composition determination apparatus as claimed in claim 1, comprising a conveyor system for moving the target relative to the apparatus such that points on a surface of the target are illuminated by x-rays once only as the target passes the apparatus.

5. A target composition determination apparatus as claimed in claim 1 wherein the x-ray emission element transmits continuous streams of x-rays.

6. A target composition determination apparatus as claimed in claim 1 which includes at least one x-ray emission element configured to transmit x-ray photons over a plurality of transmission planes.

7. A target composition determination apparatus as claimed in claim 1 wherein the detection element consists of a single transducer configured to receive x-ray photons which have interacted with the target.

8. A target composition determination apparatus as claimed in claim 1 wherein the x-ray detection element consists of an array of individual detection components, with each component being configured to detect x-rays within a band of energy values.

9. A target composition determination apparatus as claimed in claim 8 wherein the x-ray detection element is formed from an array of photodiodes configured to receive x-ray photons and provide output electrical signals.

10. A target composition determination apparatus as claimed in claim 1 wherein the processing element is configured to receive and collates at least one output signal from the x-ray detection element to indicate the number of x-ray photons interacting with the target at specific energy levels during a predefined time period.

11. A target composition determination apparatus as claimed in claim 1 wherein the processing element is configured to completes a standardisation process on a received output signal of the x-ray detection element which uses wavelength standards which provide at least two uniquely known features within the x-ray energy spectrum.

12. A target composition determination apparatus as claimed in claim 1 wherein the processing element is configured to employ a different component material for each component material to have its presence determined within the target.

13. A target composition determination apparatus as claimed in claim 1 wherein the processing element is configured to indicate that the target includes an unidentified material if the material does not correlate with the calibration used.

14. A target composition determination apparatus as claimed in claim 1 wherein the multivariate calibration is prepared for component material using specific component materials of interest against an unknown background of component materials.

15. A target composition determination apparatus as claimed in claim 1 wherein the calibration is prepared using a background spectral data set in addition to the known response patterns of at least one confounding material.

16. A target composition determination apparatus as claimed in claim 1 wherein the processing element is configured to define at least a portion of an image of the target, wherein a pixel of the portion of the image is defined by the x-ray detection element signal or signals received within a single time period.

17. A target composition determination apparatus as claimed in claim 1 wherein the processing element is configured to define a spectral representation of at least a portion of the target using a signal or signals of the x-ray detection element received within a single time period.

18. A target composition determination apparatus as claimed in claim 16 wherein the portion of the image or spectral representation is provided by a hyper cube which indicates a predicted mass of each component material associated with each pixel of the image.

19. A target composition determination apparatus as claimed in claim 16 wherein said image or spectral representation is provided by a hypercube which indicates a probability estimate for the mass predicted of each component material associated with each pixel of the image.

20. A target composition determination apparatus as claimed in claim 16 comprising an image processing unit configured to compare adjacent or nearby pixels of the portion of the image.

21. A target composition determination apparatus as claimed in claim 20 wherein the image processing unit completes a pattern detection process.

22. A target composition determination apparatus as claimed in claim 1 comprising an automatic indication alarm system.

23. A method of determining the presence of at least one component material within a target, comprising the steps of;
   i) concurrently transmitting x-ray photons with a plurality of different energy levels spanning the x-ray spectrum at the target;
   ii) receiving, at a detection element, x-ray photons which have interacted with the target
   iii) receiving at least one input signal from the detection element, said input signal or signals indicating the number of x-ray photons which have interacted with the target and the energy levels determined for each of said x-ray photons;
   iv) batching the input signal or signals over a pre-selected time period to define the physical resolution of the target composition apparatus when the target is moved relative to the apparatus;
   v) selecting input signal or signals having energy levels of greatest significance;
   vi) applying at least one multivariate calibration prepared for a particular class of targets to data relating to the number of x-rays which have interacted with the target and the energy levels determined for each of said x-rays as derived from the selected signal or signals, to determine the presence of at least one component material of interest within the target, wherein the multivariate calibration correlates the data, its variances and co-variances against one or more of: previously identified material levels, the presence of an unknown material, or the presence of an undesirable material;
   vii) indicating the presence of at least one component material within the target.

* * * * *